United States Patent [19]

Hamada et al.

[11] 4,424,390
[45] Jan. 3, 1984

[54] PROCESS FOR PRODUCING 5-HALOMETHYLFURFURAL

[75] Inventors: Kazuhiko Hamada, Ibaraki; Hiroshi Yoshihara, Takatsuki; Gohfu Suzukamo, Ibaraki, all of Japan

[73] Assignee: Sumitomo Chemical Company, Limited, Osaka, Japan

[21] Appl. No.: 437,254

[22] Filed: Oct. 28, 1982

[30] Foreign Application Priority Data

Nov. 6, 1981 [JP] Japan .................................. 56-178508

[51] Int. Cl.$^3$ ............................................. C07D 307/46
[52] U.S. Cl. ................................................... 549/483
[58] Field of Search ......................................... 549/483

[56] References Cited

U.S. PATENT DOCUMENTS 4,154,744 5/1979 Hamada et al. ...................... 549/483

OTHER PUBLICATIONS

Chemical Abstracts, vol. 82, No. 21, May 26th 1975, p. 610, No. 139941u, Columbus Ohio (USA) (Ref.=-JP-A-No. 74 20 580 (Shiono Koryo Kaisha, Ltd. 5/1974).

*Primary Examiner*—Richard Raymond
*Attorney, Agent, or Firm*—Stevens, Davis, Miller & Mosher

[57] ABSTRACT

A process for producing 5-halomethylfurfural represented by the formula,

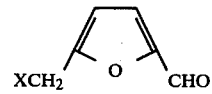

wherein X is Cl or Br, which comprises carrying out a acid-decomposition of saccharide in a water/organic solvent/magnesium halide system with hydrochloric acid, sulfuric acid, hydrogen chloride or other mineral acid in the presence or absence of surface active agent as a catalyst. The 5-halomethylfurfural is useful as an intermediate of medicines, agricultural chemicals, perfumes and the like.

8 Claims, No Drawings

PROCESS FOR PRODUCING 5-HALOMETHYLFURFURAL

The present invention pertains to an improved process for producing 5-halomethylfurfural (hereinafter referred to as "5-XMF") of general formula (I) useful as an intermediate of medicines, agricultural chemicals, perfumes and the like. More particularly, it relates to a process for producing 5-XMF by acid-decomposing saccharide such as monosaccharide, disaccharide, isomerized saccharide or the like in the reaction system of water-organic solvent-magnesium halide.

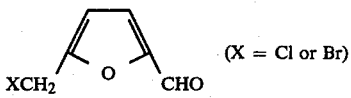
(X = Cl or Br)   (I)

As a process for producing 5-XMF, for example following processes are so far well known with reference to chlorine atom as X of the above formula:

(1) A process, wherein fructose or saccharose is treated by hydrochloric acid in the presence of carbon tetrachloride (J. Chem. Soc., 667, 1944). This process is not commercially available, because there is accompanied gelation of solvent during the reaction and operation becomes vey complicated, and it provides low yield as low as about 20%. According to the follow-up test result of this process, it is reported that large amount of humus is produced in the course of reaction, and filtration and decantation after the reaction become extremely difficult.

Therefore, there is proposed a commercially practicable process, wherein the acetoxymethyl group of 5-acetoxymethylfurfural is converted to a chloromethyl group by reaction with hydrochloric acid [Japanese Patent Publication number (examined) 39699/1970]. However, this process is not always commercially advantageous, because it necessarily requires many steps such that, for example, furfuryl alcohol, the starting material is acetylated, then formylated by Vilsmeier reacton to provide 5-acetoxymethylfurfural.

(2) Recently, a process is reported, wherein fructose or a high fructose syrup prepared by the concentration of fructose fraction in the isomerized saccharide is subjected to decomposition by hydrochloric acid in the presence of large amount of chlorobenzene. (Journal of Chemical Technology and Biotechnology, 1981, 31, 205). It is described that, by applying constant high speed stirring in this process, 5-XMF can be produced in the yield of 90-95% much higher than those of ordinary direct synthetic processes from saccharide. This process may however be almost impossible in terms of commercial production because it requires highly diluted reaction system comprising large amount of poisonous chlorobenzene and essentially the employment of constant high speed stirring. According to the follow-up test result of this process by the present inventors, it can't be helped that the process lacks reproducibility because there is much difficulties such that crude yield of 5-XMF by the method is about 80% at most and the process itself is not considered to be easily attained even by the ordinally skilled in the art, and moreover 5-XMF produced in the chlorobenzene solvent system is low in purity containing much of tar.

While, the present inventors previously found and disclosed a process for producing furan derivatives including 5-chloromethylfurfural in an advantageous yield and high selectivity from saccharides such as monosaccharide, disaccharide, etc. (U.S. Pat. No. 4,154,744).

In order to solve aforesaid various problems of the method of producing 5-chloromethylfurfural so far and to provide a more advantageous process producing 5-XMF on a commercial scale, the present inventors have intensively studied on it and have found that when saccharides such as monosaccharide (including isomerized saccharide), disaccharide are acid-decomposed in the presence or absence of a surface active agent in a water, inert organic solvent and magnesium halide system, objective 5-XMF can be obtained in a high yield and high selectivity.

One general object of the present invention is to provide 5-XMF in a high yield and high selectivity and to provide an improved production process therefor. A further object is to provide an improved process for producing 5-XMF by the acid-decomposition of saccharides in the presence or absence of a surface active agent in the new reaction system of water, inert organic solvent and magnesium halide. These and other objects and advantages of the invention will be apparent to persons skilled in the art from the following description.

The method of the invention can be carried out in the first place by mixing a raw saccharide supplied for acid decomposition with mineral acid such as hydrochloric acid in the presence of water, inert organic solvent and magnesium halide in the presence or absence of a surface active agent which is used as a catalyst. Mineral acid used in the reaction can be added in advance and also continuously or intermittently with the consumption of it in the reaction. In this case, various modification for addition of reactants and catalyst can be applied. For example, a raw saccharide can be previously dissolved in a proper amount of water and hydrochloric acid gas, etc. introduced therein. Alternatively, a raw saccharide and mineral acid can be mixed together in advance, and magnesium halide and optional surface active agent are added in this order thereto, thereafter the mixture thus prepared is added in a stirred and heated organic solvent prepared separately. In this case, reaction can proceed smoothly and operated easily. In a further alternative example, when crystalline fructose is used as a raw saccharide, it can be supplied in a paste-like fructose by mixing it with proper amount of water just like high-fructose syrup.

When the reaction is finished after a definite period of time, heating is stopped and the reaction system is cooled immediately to room temperature while stirring of the system under flow of nitrogen being continued. (If necessary, a definite amount of Celite, activated carbon can be added thereto and continued stirring of the system for about an hour). The reaction mixture cooled to room temperature is immediately filtered while being washed with a small amount of organic solvent. The separated organic layer is washed with an aqueous solution saturated with sodium chloride and dried to obtain an objective organic layer. The net yield and purity of 5-XMF produced are determined by gas chromatography (internal standard method). Thus, the apparent yield (a crude yield) is a value obtained from the definite weight which the amount of residual 5-XMF reaches finally when organic solvent is eliminated from said organic layer under reduced pressure by using, for example, a rotary evaporator and a vacuum pump, etc. The net yield is a value obtained by multiplying the apparent yield and its purity together.

The saccharides used in this invention include monosaccharide such as ketohexoses (e.g., fructose, sorbose, tagatose, etc.), and aldohexoses (e.g. glucose, galactose, mannose, etc.). However, in case of aldohexoses, the yield is generally low. As disaccharide, saccharose, maltose, lactose etc. are used. Furthermore, so-called isomerized saccharide obtained by inverting glucose with enzyme may also be used. Of these, for example, isomerized sacacharide or its fructose fraction concentrate (high fructose syrup, etc.), fructose or saccharose (cane sugar) is preferably used. These saccharides are obtainable as cheap raw material and their acid decomposition reaction proceeds easily, so that this process is industrially advantageous.

The acid used in the reaction includes hydrogen halide or its aqueous solution. Hydrohalogenic acid is generally used in a manner of addition from the outside of the reaction system, but occasionally it is generated in the reaction system in situ with the addition of other mineral acid. That is, generally, hydrogen chloride, hydrochloric acid, etc. can be used, but mineral acids other than hydrochloric acid, for example, sulfuric acid can also be used whereby the reaction can be carried out easily with hydrogen halide generated in situ in the reaction of sulfuric acid and magnesium halide present as one of the reactants in the new reaction system of the present invention under heating. The amount of acid used is generally 1 to 6 times by equivalent based on raw saccharide. There is given no specific advantage in using over 6 times by equivalent.

Magnesium halides used in the reaction are generally stable hydrates such as $MgCl_2.6H_2O$, $MgBr_2.6H_2O$, etc. and easily obtainable. Anhydrous magnesium halide may be used as it is, however, it is sparingly soluble in acid and causes exothermic reaction when it dissolves. However, it can be easily used similarly to stable hydrates with the addition of water equivalent to crystallization water. Magnesium halide is generally used in an amount of 0.5 to 4 mol, preferably 1 to 2 mol based on 1 mol of raw saccharide. When it is used more than 4 mol, insoluble material undesirably happens to be produced in the mineral acid solution. The crude purity of 5-XMF obtained in such magnesium halide addition system is not different from that obtained in the prior art non-addition system. So that there is no problem in this sense in conducting reaction in the novel system of the present invention.

The organic solvent used in the reaction includes inert organic solvent such as an aromatic hydrocarbon, an alkyl- or halogen-substituted aromatic hydrocarbon, a halogen-substituted aliphatic hydrocarbon, or a mixture thereof, that is, for example, aromatic hydrocarbon such as benzene, toluene, xylene, halogenated or nitrated derivatives thereof such as chlorobenzene, o-dichlorobenzene, nitrobenzene, aliphatic halogenated hydrocarbon such as methylene chloride, trichloroethylene, chloroform, carbon tetrachloride, or a mixture thereof. Alcohol such as methanol, ethanol, iso-propyl alcohol, ketone such as acetone, methylisobutylketone may also be used in combination with those solvents as aforesaid. Of these organic solvents, toluene, benzene, carbon tetrachloride, trichloroethylene, chlorobenzene and a mixture thereof are preferably used. The amount of organic solvent used is not generally restricted. Large amount of organic solvent per raw saccharide are advantageously used for the extraction efficiency and heat stability of 5-XMF produced. However, a smaller amount of solvent is used advantageously from a viewpoint of commercial production. Usually, 1 to 50 parts by weight of organic solvent per 1 part by weight of raw saccharide are preferably used.

The surface active agent used as a catalyst in the reaction is specifically effective for preventing gelation, formation of humus in the reaction system and makes post treatment (e.g., filtration, decantation, etc.) smooth under the condition where about 1 to 10 parts by weight of organic solvent is used per 1 part by weight of raw saccharide. However, when a large amount of organic solvent such as about 10 to 50 parts by weight of it is used per 1 part by weight of raw saccharide, the reaction system is a highly diluted system, wherein a surface active agent is optionally used according to the necessity.

The surface active agent used in the present invention includes anionic, cationic, amphoteric ionic and nonionic surface active agent. Of these, cationic, amphoteric and anionic surface active agent are particularly preferred. The cationic surface active agents include those of a quaternary ammonium salt type (e.g. lauryltrimethylammonium chloride, cetyltrimethylammonium chloride, cetyldimethylbenzylammonium chloride, tetrabutylammonium bromide, tetrabutylammonium hydrogen sulfate, etc.), and those of a quaternary phosphonium salt type (e.g., lauryltrimethylphosphonium chloride, etc.), those of a pyridinium salt type (e.g., cetylpyridinium chloride, etc.) and those of an amine salt type.

The amphoteric surface active agents include those of an amino acid type (e.g., sodium laurylaminopropionate, etc.), those of a betaine type (e.g., lauryldimethyl betaine, stearyldimethyl betaine, laurylhydroxyethyl betaine, etc.).

The anionic surface active agents include those of alkali metal salts of a higher fatty acid (e.g., sodium laurate, sodium palmitate, sodium stearate, etc.), salts of a higher alkyl sulfonic acid (e.g., sodium alkylbenzenesulfonates such as sodium laurylbenzenesulfonate, sodium dodecylbenzenesulfonate, etc.), salts of a higher alcohol sulfuric acid ester (e.g., sodium laurylsulfate, sodium cetylsulfate, sodium oleylsulfate, Teepol type salt of a secondary alcohol).

The nonionic surface active agents include those of a polyethylene glycol type (e.g., higher alcohol/ethylene oxide adducts, phenol/ethylene oxide adducts, fatty acid/ethylene oxide adducts) and those of a polyhydric alcohol type (e.g., higher fatty acid sorbitan ester, sugar ester, etc.).

These four kinds of surface active agent may be used alone or in combination thereof. When they are used in combination, such combinations as anionic/amphoteric surface active agent, cationic/amphoteric surface active agent, anionic/cationic surface active agent and the like are used. Of these combinations, mixed surface active agents such a equimolar combination as of anionic/cationic surface active agent, anionic/amphoteric surface active agent are preferably used. In these cases, the resinification is reduced with the formation of micelle-like state in the reaction system and the post treatment becomes easy. As preferable combination is exemplified such as combination as that of 1 part of a salt of a higher alkylsulfonate and 1 part of a quaternary ammonium salt, etc.

The amount of surface active agent used is 1/1000–1/10 mol, preferably 1/200–1/50 mol, based on 1 mol of said raw saccharide.

The temperature at which acid-decomposition is carried out, it not particularly limited. Of course, heating is preferred to accelerate the reaction, however, and a temperature not more than 150° C., preferably from about −10° C. to about 110° C. is suitable to inhibit side reactions. The reaction completes generally in 0.2 to 10 hours under such a temperature condition.

The characteristics of the present invention can be summed up as follows:

(1) The acid decomposition of saccharide takes place effectively and the yield is improved to a large extent when magnesium halide is added to the novel reaction system essentially consisting of water, organic solvent and surface active agent.

(2) Generally in the usual method so far wherein a high fructose syrup (i.e., so called invert sugar solution comprising enriched fructose portion provided by an isomerization process of saccharide) is used as a raw material, the yield per net fructose is lower than that in the process wherein a crystalline pure fructose is used as a raw material because of the influence of the water contained in the former (75% solid content, etc.). In the process of the present invention adding magnesium halide, however, a reduction in the yield as aforesaid is not observed under the same condition, and besides this process is advantageous in terms of material cost.

(3) Magnesium halide used as an additive is cheap and besides gives no disadvantage for post treatment, thus causing no problems in neutralization, treatment of waste water and the like.

(4) When hydrochloric acid or hydrogen chloride is used, dehydration and chlorine-substitution of saccharides take place to obtain an objective 5-chloromethyl-furfural as 5-XMF. The combination of magnesium halide and mineral acid such as sulfuric acid other than hydrogen halide also serves as an hydrogen halide or hydrohaloic acid. Thus, for example, sulfuric acid reacts with magnesium halide present in the reaction system in situ and generates hydrogen halide which decomposes said saccharide to produce objective 5-XMF. In this case, there may be employed either of a process in which sulfuric acid is added dropwise to a saccharide/water/organic solvent/magnesium halide system or a process in which a saccharide/water/magnesium halide system is added dropwise to a sulfuric acid/organic solvent system.

It is of great significance that 5-XMF, one of the important intermediate of medicines, agricultural chemicals, perfumes and the like can be commercially produced from saccharides which are cheap and reproducible as a raw material according to the knowledge of the present invention. For example, 5-chloromethylfurfural can be produced by acid decomposition of saccharides specifically in the mixture of saccharide, water, organic solvent and magnesium chloride. 5-Propargyl furfuryl alcohol can be derived from 5-chloromethylfurfural and gives the pyrethroid compounds which are important as excellent insecticides.

The present invention will be illustrated in more detail with reference to the following examples, which are not however intended to limit the invention thereto.

EXAMPLE 1

To a four-necked cylindrical separable flask equipped with a condenser, a stirrer, a nitrogen gas inlet tube, a dropping funnel and a baffle, was introduced 150 ml of toluene. The temperature of the water bath was set at 75° C. while introducing a nitrogen gas with slow stirring of toluene. Thereafter, to the stirred toluene layer was added 24.22 g of high fructose-syrup F-900 (Grade No. of Sanwa Denpun Kogyo Co.) (solid content, 75.8 wt%; fructose content, 90 wt%) and 20.74 g of magnesium chloride hexahydrate $MgCl_2.6H_2O$ (one equivalent based on the fed net fructose) in this order. This emulsion system comprising high fructose, magnesium chloride and toluene was stirred at 75° C. for about 30 minutes at 400 r.p.m.

During that period, the position of the mixing blade in the solution was adjusted so as to prevent the generation of bubbles on the surface of the stirred solution as well as the splashing and attachment of the stirred solution on the side wall or upper part of the flask. Thereafter, 31.92 g of 35 wt% hydrochloric acid (three equivalents based on the fed net fructose) was added dropwise in two minutes via a dropping funnel to the solution stirred at 400 r.p.m. After the reaction mixture was left to react for 1 hour at 75° C., heating was stopped and the reaction mixture was immediately cooled to room temperature (about 25° C.). During that period, stirring of the solution was continued in nitrogen gas atmosphere. After stopping stirring and allowing the reaction solution to stand, the solution was suction-filtered. A small amount of formed humus was washed with toluene which was once used for washing of the flask, mixing blade and the like. The filtrate after being left to stand was separated to recover a toluene layer. This organic layer was washed twice with an aqueous solution saturated with sodium chloride and dried over magnesium sulfate. The net yield and purity of formed 5-chloromethylfurfural were determined by gas chromatography (internal standard method). The apparent yield (crude yield) was determined from a value when crude 5-chloromethylfurfural, which is a residue obtained by removing the organic solvent from the organic layer above under reduced pressure (by means of a rotary evaporator and a vacuum pump), had reached definite weight. The result was as follows:

The amount of 5-chloromethylfurfural obtained, was 11.6 g (yield, 87.5%). The product can be purified easily to not less than 95% of purity by purification treatment with a small amount of activated carbon. This is the same in the following examples.

EXAMPLE 2

150 Ml of toluene was introduced to the same flask as used in Example 1, and while introducing a nitrogen gas with slow stirring of toluene, the temperature of the water bath was set at 75° C. Thereafter, a paste-like liquid prepared by well-mixing 18.0 g of crystalline fructose with 2.2 g of water, and then 20.4 g (one equivalent based on the fed fructose) of $MgCl_2.6H_2O$ were successively added to the stirred toluene layer. After completion of the addition, stirring was carried out at 400 r.p.m. for about 30 minutes. Thereafter, 31.4 g of 35% hydrochloric acid was added dropwise in 5 minutes from the dropping funnel to the stirred solution. After completion of the dropwise addition, stirring was continued at 400 r.p.m. at 75° C. for 1 hour, at which point heating was stopped and the reaction system was immediately lowered to room temperature (about 25° C.). During that period, stirring was still continued. After standing at room temperature, the post treatment of the solution was carried out in the same manner as in Example 1 and was obtained 12.5 g (yield 86.6%) of 5-chloromethylfurfural as product.

EXAMPLE 3

One hundred milliliters of toluene was introduced to the same flask as in Example 1, and the temperature of the water bath was set at 80° C. with slow stirring of toluene. Separately, 15.0 g of crystalline fructose, 16.9 g of $MgCl_2.6H_2O$, 0.2 of Quartamin-24P, a surface active agent (27.5% aqueous solution of lauryltrimethylammonium chloride; a trade name of Kao-Atlas Co.) and 34.8 g of 35% hydrochloric acid were successively added to a round-bottom flask, and the mixture was stirred at 300 r.p.m. at room temperature for about 30 minutes to obtain a mixed liquid containing dissolved $MgCl_2.6H_2O$. This mixed liquid (yellowish brown) was added dropwise in about 15 minutes from the dropping funnel to the toluene layer stirred at 300 r.p.m. in the flask which was held in the water bath set at 80° C. After completion of the dropwise addition, stirring was continued at 300 r.p.m. for about 15 minutes. Thereafter, heating was stopped, and the reaction system was immediately lowered to room temperature with stirring. After standing, the reaction solution was treated in the same manner as in Example 1. The result was as shown below.

The amount of 5-chloromethylfurfural obtained, 10.0 g (yield, 83.1%).

EXAMPLE 4

Procedure was carried out in approximately the same manner as in Example 1 except that 20.4 g of hydrogen chloride gas as an acid for acid-decomposition, was introduced into the reaction system over 30 minutes. The reaction condition and result were shown in Table 1.

EXAMPLE 5

Procedure was carried out in approximately the same manner as in Example 1 except that 500 ml of chlorobenzene was used as organic solvent, and that 32.4 g of 35% hydrochloric acid and 10.3 g of hydrogen chloride gas were introduced, as an acid for acid-decomposition, into the reaction system over 2 minutes and 30 minutes, respectively. The reaction conditions and results were shown in Table 1.

EXAMPLE 6

Procedure was carried out in the same manner as in Example 3 except that 0.08 g of cetylmethylammonium chloride and 0.09 g of sodium laurylbenzenesulfonate were used as surface active agent in place of Quartamin-24P. The reaction condition and result were shown in Table 1.

EXAMPLE 7

Procedure was carried out in approximately the same manner as in Example 1 except that 400 ml of o-dichlorobenzene was used as organic solvent. The reaction condition and result were shown in Table 1. The yield was determined by gas chromatography.

EXAMPLE 8

Procedure was carried out in approximately the same manner as in Example 2 except that 400 ml of trichloroethylene was used as organic solvent. The reaction condition and result were shown in Table 1.

EXAMPLE 9

Procedure was carried out in approximately the same manner as in Example 2 except that crystalline saccharose was used as saccharide. The reaction condition and result were shown in Table 1.

EXAMPLE 10

Procedure was carried out in approximately the same manner as in Example 2 except that crystalline glucose was used as saccharide, and that 31.4 g of 35% hydrochloric acid and 11.9 g of hydrogen chloride gas were introduced, as an acid for acid-decomposition, over 5 minutes and 30 minutes respectively. The reaction condition and result were shown in Table 1.

COMPARATIVE EXAMPLE 1

Procedure was carried out in approximately the same manner as in Example 3 except that $MgCl_2.6H_2O$ was not used. The reaction condition and result were shown in Table 1.

TABLE 1

| Example No. | Kind of saccharide Amount (g) | Kind of additive Amount (g) | Organic solvent Amount (ml) | Acid Amount (g) | Reaction condition | | | 5-Chloromethylfurfural | |
|---|---|---|---|---|---|---|---|---|---|
| | | | | | Number of rotations (r.p.m.) | Temperature (°C.) | Time (hr) | Amount (g) | Yield (%) |
| 4 | High fructose. syrup F-900 (24.6) | $MgCl_2.6H_2O$ (20.8) | Toluene (300) | Hydrogen chloride gas (20.4) | 1200 | 75 | 1.0 | 12.3 | 91.4 |
| 5 | High fructose. syrup F-900 (24.6) | $MgCl_2.6H_2O$ (20.8) | Chlorobenzene (500) | 35% Hydrochloric acid (32.4) + Hydrogen chloride gas (10.3) | 1200 | 75 | 1.0 | 12.4 | 92.1 |
| 6 | Crystalline fructose (15.0) | $MgCl_2.6H_2O$ (16.9) + Cetyltrimethylammonium chloride (0.08) Sodium laurylbenzenesulfonate (0.09) | Toluene (100) | 35% Hydrochloric acid (34.8) | 300 | 80 | 0.5 | 10.2 | 84.7 |
| 7 | High fructose. syrup F-900 (24.6) | $MgCl_2.6H_2O$ (20.8) | o-Dichlorobenzene (400) | 35% Hydrochloric acid (32.2) | 1800 | 75 | 1.0 | — | 89.5 |
| 8 | Crystalline | $MgCl_2.6H_2O$ (20.4) | Trichloro- | 35% | 1500 | 75 | 1.0 | — | 82.8 |

TABLE 1-continued

| Example No. | Kind of saccharide Amount (g) | Kind of additive Amount (g) | Organic solvent Amount (ml) | Acid Amount (g) | Reaction condition | | | 5-Chloromethyl-furfural | |
|---|---|---|---|---|---|---|---|---|---|
| | | | | | Number of rotations (r.p.m.) | Temperature (°C.) | Time (hr) | Amount (g) | Yield (%) |
| | fructose (18.0). Water (5.0) | | ethylene (400) | Hydrochloric Acid (31.4) | | | | | |
| 9 | Crystalline saccharose (18.0). water (5.0) | MgCl$_2$.6H$_2$O (20.4) | Toluene (500) | 35% Hydrochloric acid (31.4) | 800 | 70 | 10.0 | 10.4 | 68.5 |
| 10 | Crystalline glucose (18.0). water (5.0) | MgCl$_2$.6H$_2$O (20.4) | Toluene (600) | 35% Hydrochloric acid (31.4) + Hydrogen chloride gas (11.9) | 800 | 75 | 24.0 | 8.3 | 57.5 |
| Comparative example 1 | High fructose. syrup F-900 (24.6) | Quartamin-24P (0.2) | Toluene (150) | 35% Hydrochloric acid (32.4) | 300 | 80 | 0.5 | 9.6 | 71.3 |

EXAMPLE 11

To the same flask as used in Example 1 was introduced 150 ml of toluene, and while introducing a nitrogen gas with slow stirring of toluene, the temperature of the water bath was set at 75° C. Thereafter, a paste-like liquid prepared by well mixing 18.0 g of crystalline fructose and 5.0 g of water, and 40.6 g (two equivalents based on the fed fructose) of MgCl$_2$.6H$_2$O were successively added to the toluene layer with stirring at 1800 r.p.m. Thereafter, 20.2 g of 97% conc. sulfuric acid (two equivalents based on the fed fructose) was added dropwise in 5 minutes from the dropping funnel to the solution stirred at 1800 r.p.m. Stirring was continued at 1800 r.p.m. and at 75° C. for 1 hour, at which points heating was stopped and the reaction system was immediately lowered to room temperature (about 25° C.). During that period, stirring was continued. Stirring was then stopped and the reaction solution was allowed to stand. Thereafter, a small amount of water was added to the solution which was then suction-filtered. The subsequent post treatment was carried out in the same manner as in Example 1.

The result was as shown below.

The amount of 5-chloromethylfurfural obtained, 12.4 g (yield 85.9%).

EXAMPLE 12

To the same flask as used in Example 1 were introduced 200 ml of toluene and 28.0 g of 70% conc. sulfuric acid, and while introducing a nitrogen gas with stirring, the temperature of the water bath was set at 75° C. A syrup-like liquid prepared by well mixing 18.5 g of crystalline fructose, 10.3 g of water and 41.8 g of MgCl$_2$.6H$_2$O, was added dropwise at 75° C. over 1 hour to the toluene/sulfuric acid solution stirred at 1800 r.p.m. After dropwise addition, temperature-maintenance and stirring (1800 r.p.m.) were continued for 1 hour. Thereafter, heating was stopped and the reaction system was immediately lowered to room temperature (about 25° C.). The subsequent operation was carried out in the same manner as in Example 1.

The result was as shown below.

The amount of 5-chloromethylfulfural obtained, 13.2 g (yield 88.9%).

EXAMPLE 13

Procedure was carried out in approximately the same manner as in Example 12 except that 500 ml of chlorobenzene was used as organic solvent. The reaction condition and result were shown in Table 2. The product is 5-chloromethylfurfural.

EXAMPLE 14

Procedure was carried out in approximately the same manner as in Example 11 except that 58.4 g of magnesium bromide hexahydrate, MgBr$_2$.6H$_2$O was used as magnesium halide, and that 400 ml of chlorobenzene was used as organic solvent. The reaction condition and result were shown in Table 2. The product is 5-bromomethylfurfural.

EXAMPLE 15

Procedure was carried out in approximately the same manner as in Example 12 except that 58.4 g of MgBr$_2$.6H$_2$O was used as magnesium halide. The reaction condition and result were shown in Table 2. The product is 5-bromomethylfurfural.

TABLE 2

| Example No. | Kind of saccharide Amount (g) | Kind of additive Amount (g) | Organic solvent Amount (ml) | Acid Amount (g) | Reaction condition | | | 5-Halomethyl-furfural | |
|---|---|---|---|---|---|---|---|---|---|
| | | | | | Number of rotations (r.p.m.) | Temperature (°C.) | Time (hr) | Amount (g) | Yield (%) |
| 13 | Crystalline fructose (18.8) + water (10.4) | MgCl$_2$.6H$_2$O (42.4) | Chlorobenzene (500) | 70% Sulfuric acid (28.0) | 3500 | 75 | 2.0 | 14.0 | 92.7 |

TABLE 2-continued

| Example No. | Kind of saccharide Amount (g) | Kind of additive Amount (g) | Organic solvent Amount (ml) | Acid Amount (g) | Reaction condition Number of rotations (r.p.m.) | Temperature (°C.) | Time (hr) | 5-Halomethyl-furfural Amount (g) | Yield (%) |
|---|---|---|---|---|---|---|---|---|---|
| 14 | Crystalline fructose (18.0) + water (5.0) | MgBr$_2$.6H$_2$O (58.4) | Chlorobenzene (400) | 97% Sulfuric acid (20.2) | 3500 | 50 | 3.0 | 15.8 | 83.8 |
| 15 | Crystalline fructose (18.0) + water (5.0) | MgBr$_2$.6H$_2$O (58.4) | Toluene (500) | 70% Sulfuric acid (29.0) | 1800 | 50 | 4.0 | 16.5 | 87.5 |

What is claimed is:

1. A process for producing 5-halomethylfurfural represented by the formula (I),

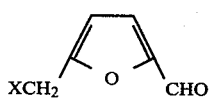 (I)

wherein X is Cl or Br, which comprises carrying out an acid-decomposition of saccharide in a water/organic solvent/magnesium halide system, in the presence or absence of a surface active agent as a catalyst.

2. A process according to claim 1, wherein said saccharide is isomerized saccharide, its fructose concentrate, fructose or saccharose (cane sugar).

3. A process according to claim 1, wherein acid used for said acid-decomposition of saccharide is hydrochloric acid, sulfuric acid, or hydrogen chloride.

4. A process according to claim 1, wherein said organic solvent is an aromatic hydrocarbon, an alkyl- or halogen-substituted aromatic hydrocarbon, a halogen-substituted aliphatic hydrocarbon, or a mixture thereof.

5. A process according to claim 1, wherein said organic solvent is toluene, benzene, carbon tetrachloride, trichloroethylene, chlorobenzene or a mixture thereof.

6. A process according to claim 1, wherein said magnesium halide is magnesium chloride.

7. A process according to claim 1, wherein sulfuric acid is added to the reaction system to generate hydrogen halide as an acid for acid-decomposition.

8. A process according to claim 1, wherein a saccharide/water/magnesium halide system is added dropwise to sulfuric acid/organic solvent system to carry out the acid-decomposition of saccharide.

* * * * *